US006777587B1

(12) United States Patent
Bisaro

(10) Patent No.: US 6,777,587 B1
(45) Date of Patent: Aug. 17, 2004

(54) METHOD OF ENHANCING PLANT RESISTANCE TO GEMINIVIRUSES BY TRANSFORMATION WITH A SNF-1 POLYNUCLEOTIDE

(75) Inventor: David M. Bisaro, Dublin, OH (US)

(73) Assignee: Ohio State University Research Foundation, Columbus, OH (US)

( * ) Notice: Subject to any disclaimer, the term of this patent is extended or adjusted under 35 U.S.C. 154(b) by 152 days.

(21) Appl. No.: 09/633,328

(22) Filed: Aug. 7, 2000

Related U.S. Application Data

(60) Provisional application No. 60/147,613, filed on Aug. 6, 1999.

(51) Int. Cl.[7] .......................... C12N 5/09; C12N 15/29; C12N 15/31; C12N 15/82; A01H 5/00

(52) U.S. Cl. ....................... 800/279; 800/278; 800/306; 800/298; 800/295; 800/320.1; 800/320.2; 800/320.3; 800/320; 800/317.2; 800/317.3; 800/312

(58) Field of Search ................................ 800/278, 279, 800/306, 298, 295, 320.1, 320, 320.2, 320.3, 320.4, 317.2, 317.3, 317.4, 312; 536/23.1, 23.6, 23.7; 435/419, 468

(56) References Cited

U.S. PATENT DOCUMENTS 5,648,599 A 7/1997 Tanksley et al.

OTHER PUBLICATIONS

Lazar et al, Transforming Growth Factor x: Mutation of Aspartic Acid 47 and Leucine 48 Results in Different Biological Activities, Mar. 1988, Molecular and Cellular Biology, vol. 8 No. 3, pp. 1247–1252.*

Broun et al, Catalytic Plasticity of Fatty Acid Modification Enzymes Underlying Chemical Diversity of Plant Lipids, Nov. 1998, Science vol. 282, pp. 1315–1317.*

Lacombe et al, "The Identity of Plant Glutamate Receptors", May 2001, Science vol. 292, pp. 1486–1487.*

Ryals et al, "Systemic Acquired Resistance", Oct. 1996, The Plant Cell, vol. 8, pp. 1809–1819.*

GenBank Accession No. X94755, 1996.*

"Gene Regulation in Geminivirus" by Bisaro, International Workshop on Bemisia and Geminiviruses, San Jan, Puerto Rico, Jun. 7–12, 1998.

"The Role of Geminivirus Protein (TrAP) in Host Defence Suppression" by Bisaro, et al., The Thirteenth John Innes Symposium, Norfolk, UK, Jul. 20–23, 1999.

"Geminvirus Transactivator May Disable a Host Defense Response" by Bisaro, et al., 7$^{th}$ International Congress of Plant Pathology, Edinburgh, Scotland, Aug. 9–16, 1998.

"Structure and expression of a gene from *Arabidopsis thaliana* encoding a protein related to SNF1 protein kinase" by LeGuen, et al., *Gene*, 120 (1992) 249–254.

"Regulatory interaction of PRL1 WD protein with Arabidopsis SNF1–like protein kinase" by Bhalerao, et al., *Proc. natl. Acad. Sci. USA*, vol. 96, pp. 5323–5327, Apr. 1999.

"Two SNF1–Related Protein Kinases from Spinach Leaf Phosphorylate and Inactivate 1–Hydroxy–3–Methylgluataryl–Coenzyme A Reductase, Nitrate Reductase, and Sucrose Phosphate Synthase in Vitro" by Sugden, et al., *Plant Physiology*, May 1999, vol. 120, pp. 257–274.

* cited by examiner

*Primary Examiner*—Amy J. Nelson
*Assistant Examiner*—Medina A. Ibrahim
(74) *Attorney, Agent, or Firm*—Calfee, Halter & Griswold LLP

(57) ABSTRACT

The present invention relates to a method of preparing transformed plant cells which are resistant to infection by a Geminivirus, comprising transforming said plant cells with a DNA construct comprising a polynucleotide that encodes a plant or yeast SNF-1 protein kinase and is operably linked to a promoter, and expressing said SNF-1 protein kinase in said plant cells. Also disclosed is a method for conferring viral resistance to plants, comprising regenerating the transformed plant cells to produce transgenic plants that express the SNF-1 kinase and are resistant to infection by Geminivirus.

8 Claims, 9 Drawing Sheets

Figure 1

AKIN11 -> 1-phase Translation

```
DNA sequence    1539 b.p.   atggatcattca ... cgtgtgatctga   linear

1/1                                         31/11
atg gat cat tca tca aat aga ttt ggc aat aat gga gtg gaa tcg att tta ccg aat tac
M   D   H   S   S   N   R   F   G   N   N   G   V   E   S   I   L   P   N   Y
61/21                                       91/31
aag ctt ggt aaa act ctt gga att ggg tct ttt ggg aag gtg aaa ata gca gag cat gtt
K   L   G   K   T   L   G   I   G   S   F   G   K   V   K   I   A   E   H   V
121/41                                      151/51
gtc aca ggg cat aag gtt gct atc aaa atc ctt aat cgt cgt aag atc aag aac atg gag
V   T   G   H   K   V   A   I   K   I   L   N   R   R   K   I   K   N   M   E
181/61                                      211/71
atg gaa gag aaa gtg agg agg gag att aag att cta cgg ttg ttt atg cat cct cat att
M   E   E   K   V   R   R   E   I   K   I   L   R   L   F   M   H   P   H   I
241/81                                      271/91
att cgg cag tat gag gta ata gag acc acg agt gac att tat gtt gtg atg gag tat gtc
I   R   Q   Y   E   V   I   E   T   T   S   D   I   Y   V   V   M   E   Y   V
301/101                                     331/111
aag tct gga gag ctc ttt gat tat att gtt gag aaa ggc aga tta caa gaa gat gag gct
K   S   G   E   L   F   D   Y   I   V   E   K   G   R   L   Q   E   D   E   A
361/121                                     391/131
cgt aac ttt ttc cag cag ata ata tct ggt gta gag tac tgc cat cgt aat atg gtt gtc
R   N   F   F   Q   Q   I   I   S   G   V   E   Y   C   H   R   N   M   V   V
421/141                                     451/151
cat aga gac ctg aag cct gag aat tta cta ttg gat tcg agg tgt aat att aag att gca
H   R   D   L   K   P   E   N   L   L   L   D   S   R   C   N   I   K   I   A
```

Figure 1 (continued)

```
481/161                                 511/171
gac ttt ggg ttg agt aat gtt atg cgg gat ggt cat ttt cta aag acg agt tgt gga agc
D   F   G   L   S   N   V   M   R   D   G   H   F   L   K   T   S   C   G   S
541/181                                 571/191
ccc aac tac gct gct ccc gag gtt ata tca ggt aaa tta tat gct gga cct gaa gta gat
P   N   Y   A   A   P   E   V   I   S   G   K   L   Y   A   G   P   E   V   D
601/201                                 631/211
gta tgg agt tgc gga gtt ata ttg tac gct cta tta tgc ggt act ctt cct ttt gat gat
V   W   S   C   G   V   I   L   Y   A   L   L   C   G   T   L   P   F   D   D
661/221                                 691/231
gaa aac att ccc aac ctt ttc aag aaa att aag ggt ggg att tac act ctt cca agt cat
E   N   I   P   N   L   F   K   K   I   K   G   G   I   Y   T   L   P   S   H
721/241                                 751/251
tta tca tct gag gct aga gac ctg atc cca agg atg ctt ata gtt gac ccg gtg aaa cga
L   S   S   E   A   R   D   L   I   P   R   M   L   I   V   D   P   V   K   R
781/261                                 811/271
atc acc att cct gag atc cgt caa cac cgt tgg ttc cag act cat ctc cct cgt tat ctt
I   T   I   P   E   I   R   Q   H   R   W   F   Q   T   H   L   P   R   Y   L
841/281                                 871/291
gct gtc tct cca ccg gat aca gta gag cag gct aaa aag atc aat gag gag ata gtt caa
A   V   S   P   P   D   T   V   E   Q   A   K   K   I   N   E   E   I   V   Q
901/301                                 931/311
gaa gtg gtt aac atg gga ttt gat aga aac cag gtt ttg gaa tct cta cgc aac aga aca
E   V   V   N   M   G   F   D   R   N   Q   V   L   E   S   L   R   N   R   T
961/321                                 991/331
caa aac gat gct act gtt aca tac tac ctg tta ttg gat aac cgg ttc cgt gtt cca agt
Q   N   D   A   T   V   T   Y   Y   L   L   L   D   N   R   F   R   V   P   S
```

Figure 1 (continued)

```
1021/341                                1051/351
ggc tat cta gaa tcc gag ttt cag gag aca aca gac agt ggt tcc aat cct atg cgc aca
G   Y   L   E   S   E   F   Q   E   T   T   D   S   G   S   N   P   M   R   T
1081/361                                1111/371
cct gaa gcg ggc gct tca cct gta ggc cac tgg att cct gca cat gtg gat cac tac ggg
P   E   A   G   A   S   P   V   G   H   W   I   P   A   H   V   D   H   Y   G
1141/381                                1171/391
ttg gga gca aga tca caa gtc cct gtt gat cga aaa tgg gct ctt gga ctt cag tct cat
L   G   A   R   S   Q   V   P   V   D   R   K   W   A   L   G   L   Q   S   H
1201/401                                1231/411
gcg cat cct cgt gaa atc atg aat gaa gtt ttg aaa gct ctt caa gaa ctc aat gtg tgt
A   H   P   R   E   I   M   N   E   V   L   K   A   L   Q   E   L   N   V   C

1261/421                                1291/431
tgg aag aag att ggt cac tac aac atg aaa tgt cga tgg gtt cct ggt tta gct gat ggt
W   K   K   I   G   H   Y   N   M   K   C   R   W   V   P   G   L   A   D   G
1321/441                                1351/451
cag aat act atg gtc aac aat cag ctg cac ttc aga gat gaa tcc agc atc att gag gat
Q   N   T   M   V   N   N   Q   L   H   F   R   D   E   S   S   I   I   E   D
1381/461                                1411/471
gac tgt gcc atg act tca ccc act gtc atc aaa ttt gaa ctt cag cta tac aaa gcc cgg
D   C   A   M   T   S   P   T   V   I   K   F   E   L   Q   L   Y   K   A   R
1441/481                                1471/491
gaa gag aag tac ttg ctg gat ata cag aga gtt aac ggt ccg cag ttt ctc ttc ttg gat
E   E   K   Y   L   L   D   I   Q   R   V   N   G   P   Q   F   L   F   L   D
1501/501                                1531/511
cta tgc gcc gcc ttt ctt aca gag ctt cgt gtg atc tga
L   C   A   A   F   L   T   E   L   R   V   I   *
```

Figure 3

_Mean latent period following BCTV inoculation of transgenic antisense SNF1 plants_

| | *N. benthamiana* line | | | |
|---|---|---|---|---|
| Virus | Non-transgenic | AS-4 | AS-5 | AS-12 |
| BCTV | 21.17 +/- 1.35 (6/14) | 16.4 +/- 1.29 (14/15) | 14.7 +/- 0.87 (10/16) | 14.63 +/- 0.84 (13/14) |

SEQUENCE LISTING

```
<160> NUMBER OF SEQ ID NOS: 8

<210> SEQ ID NO 1
<211> LENGTH: 1539
<212> TYPE: DNA
<213> ORGANISM: Arabidopsis thaliana
<220> FEATURE:
<221> NAME/KEY: CDS
<222> LOCATION: (1)..(1536)

<400> SEQUENCE: 1

atg gat cat tca tca aat aga ttt ggc aat aat gga gtg gaa tcg att       48
Met Asp His Ser Ser Asn Arg Phe Gly Asn Asn Gly Val Glu Ser Ile
1               5                   10                  15

tta ccg aat tac aag ctt ggt aaa act ctt gga att ggg tct ttt ggg       96
Leu Pro Asn Tyr Lys Leu Gly Lys Thr Leu Gly Ile Gly Ser Phe Gly
            20                  25                  30

aag gtg aaa ata gca gag cat gtt gtc aca ggg cat aag gtt gct atc      144
Lys Val Lys Ile Ala Glu His Val Val Thr Gly His Lys Val Ala Ile
        35                  40                  45

aaa atc ctt aat cgt cgt aag atc aag aac atg gag atg gaa gag aaa      192
Lys Ile Leu Asn Arg Arg Lys Ile Lys Asn Met Glu Met Glu Glu Lys
    50                  55                  60
```

-continued

```
gtg agg agg gag att aag att cta cgg ttg ttt atg cat cct cat att       240
Val Arg Arg Glu Ile Lys Ile Leu Arg Leu Phe Met His Pro His Ile
65                  70                  75                  80

att cgg cag tat gag gta ata gag acc acg agt gac att tat gtt gtg       288
Ile Arg Gln Tyr Glu Val Ile Glu Thr Thr Ser Asp Ile Tyr Val Val
                85                  90                  95

atg gag tat gtc aag tct gga gag ctc ttt gat tat att gtt gag aaa       336
Met Glu Tyr Val Lys Ser Gly Glu Leu Phe Asp Tyr Ile Val Glu Lys
            100                 105                 110

ggc aga tta caa gaa gat gag gct cgt aac ttt ttc cag cag ata ata       384
Gly Arg Leu Gln Glu Asp Glu Ala Arg Asn Phe Phe Gln Gln Ile Ile
        115                 120                 125

tct ggt gta gag tac tgc cat cgt aat atg gtt gtc cat aga gac ctg       432
Ser Gly Val Glu Tyr Cys His Arg Asn Met Val Val His Arg Asp Leu
    130                 135                 140

aag cct gag aat tta cta ttg gat tcg agg tgt aat att aag att gca       480
Lys Pro Glu Asn Leu Leu Leu Asp Ser Arg Cys Asn Ile Lys Ile Ala
145                 150                 155                 160

gac ttt ggg ttg agt aat gtt atg cgg gat ggt cat ttt cta aag acg       528
Asp Phe Gly Leu Ser Asn Val Met Arg Asp Gly His Phe Leu Lys Thr
                165                 170                 175

agt tgt gga agc ccc aac tac gct gct ccc gag gtt ata tca ggt aaa       576
Ser Cys Gly Ser Pro Asn Tyr Ala Ala Pro Glu Val Ile Ser Gly Lys
            180                 185                 190

tta tat gct gga cct gaa gta gat gta tgg agt tgc gga gtt ata ttg       624
Leu Tyr Ala Gly Pro Glu Val Asp Val Trp Ser Cys Gly Val Ile Leu
        195                 200                 205

tac gct cta tta tgc ggt act ctt ccc ttt gat gat gaa aac att ccc       672
Tyr Ala Leu Leu Cys Gly Thr Leu Pro Phe Asp Asp Glu Asn Ile Pro
    210                 215                 220

aac ctt ttc aag aaa att aag ggt ggg att tac act ctt cca agt cat       720
Asn Leu Phe Lys Lys Ile Lys Gly Gly Ile Tyr Thr Leu Pro Ser His
225                 230                 235                 240

tta tca tct gag gct aga gac ctg atc cca agg atg ctt ata gtt gac       768
Leu Ser Ser Glu Ala Arg Asp Leu Ile Pro Arg Met Leu Ile Val Asp
                245                 250                 255

ccg gtg aaa cga atc acc att cct gag atc cgt caa cac cgt tgg ttc       816
Pro Val Lys Arg Ile Thr Ile Pro Glu Ile Arg Gln His Arg Trp Phe
            260                 265                 270

cag act cat ctc cct cgt tat ctt gct gtc tct cca ccg gat aca gta       864
Gln Thr His Leu Pro Arg Tyr Leu Ala Val Ser Pro Pro Asp Thr Val
        275                 280                 285

gag cag act aaa aag atc aat gag gag ata gtt caa gaa gtg gtt aac       912
Glu Gln Thr Lys Lys Ile Asn Glu Glu Ile Val Gln Glu Val Val Asn
    290                 295                 300

atg gga ttt gat aga aac cag gtt ttg gaa tct cta cgc aac aga aca       960
Met Gly Phe Asp Arg Asn Gln Val Leu Glu Ser Leu Arg Asn Arg Thr
305                 310                 315                 320

caa aac gat gct act gtt aca tac tac ctg tta ttg gat aac cgg ttc      1008
Gln Asn Asp Ala Thr Val Thr Tyr Tyr Leu Leu Leu Asp Asn Arg Phe
                325                 330                 335

cgt gtt cca agt ggc tat cta gaa tcc gag ttt cag gag aca aca gac      1056
Arg Val Pro Ser Gly Tyr Leu Glu Ser Glu Phe Gln Glu Thr Thr Asp
            340                 345                 350

agt ggt tcc aat cct atg cgc aca cct gaa gcg ggc gct tca cct gta      1104
Ser Gly Ser Asn Pro Met Arg Thr Pro Glu Ala Gly Ala Ser Pro Val
        355                 360                 365

ggc cac tgg att cct gca cat gtg gat cac tac ggg ttg gga gca aga      1152
Gly His Trp Ile Pro Ala His Val Asp His Tyr Gly Leu Gly Ala Arg
    370                 375                 380
```

-continued

```
tca caa gtc cct gtt gat cga aaa tgg gct ctt gga ctt cag tct cat      1200
Ser Gln Val Pro Val Asp Arg Lys Trp Ala Leu Gly Leu Gln Ser His
385                 390                 395                 400

gcg cat cct cgt gaa atc atg aat gaa gtt ttg aaa gct ctt caa gaa      1248
Ala His Pro Arg Glu Ile Met Asn Glu Val Leu Lys Ala Leu Gln Glu
                405                 410                 415

ctc aat gtg tgt tgg aag aag att ggt cac tac aac atg aaa tgt cga      1296
Leu Asn Val Cys Trp Lys Lys Ile Gly His Tyr Asn Met Lys Cys Arg
            420                 425                 430

tgg gtt cct ggt tta gct gat ggt cag aat act atg gtc aac aat cag      1344
Trp Val Pro Gly Leu Ala Asp Gly Gln Asn Thr Met Val Asn Asn Gln
        435                 440                 445

ctg cac ttc aga gat gaa tcc agc atc att gag gat gac tgt gcc atg      1392
Leu His Phe Arg Asp Glu Ser Ser Ile Ile Glu Asp Asp Cys Ala Met
    450                 455                 460

act tca ccc act gtc atc aaa ttt gaa ctt cag cta tac aaa gcc cgg      1440
Thr Ser Pro Thr Val Ile Lys Phe Glu Leu Gln Leu Tyr Lys Ala Arg
465                 470                 475                 480

gaa gag aag tac ttg ctg gat ata cag aga gtt aac ggt ccg cag ttt      1488
Glu Glu Lys Tyr Leu Leu Asp Ile Gln Arg Val Asn Gly Pro Gln Phe
                485                 490                 495

ctc ttc ttg gat cta tgc gcc gcc ttt ctt aca gag ctt cgt gtg atc      1536
Leu Phe Leu Asp Leu Cys Ala Ala Phe Leu Thr Glu Leu Arg Val Ile
            500                 505                 510

tga                                                                  1539


<210> SEQ ID NO 2
<211> LENGTH: 512
<212> TYPE: PRT
<213> ORGANISM: Arabidopsis thaliana

<400> SEQUENCE: 2

Met Asp His Ser Ser Asn Arg Phe Gly Asn Asn Gly Val Glu Ser Ile
1               5                   10                  15

Leu Pro Asn Tyr Lys Leu Gly Lys Thr Leu Gly Ile Gly Ser Phe Gly
            20                  25                  30

Lys Val Lys Ile Ala Glu His Val Val Thr Gly His Lys Val Ala Ile
        35                  40                  45

Lys Ile Leu Asn Arg Arg Lys Ile Lys Asn Met Glu Met Glu Glu Lys
    50                  55                  60

Val Arg Arg Glu Ile Lys Ile Leu Arg Leu Phe Met His Pro His Ile
65                  70                  75                  80

Ile Arg Gln Tyr Glu Val Ile Glu Thr Thr Ser Asp Ile Tyr Val Val
                85                  90                  95

Met Glu Tyr Val Lys Ser Gly Glu Leu Phe Asp Tyr Ile Val Glu Lys
            100                 105                 110

Gly Arg Leu Gln Glu Asp Glu Ala Arg Asn Phe Phe Gln Gln Ile Ile
        115                 120                 125

Ser Gly Val Glu Tyr Cys His Arg Asn Met Val Val His Arg Asp Leu
    130                 135                 140

Lys Pro Glu Asn Leu Leu Leu Asp Ser Arg Cys Asn Ile Lys Ile Ala
145                 150                 155                 160

Asp Phe Gly Leu Ser Asn Val Met Arg Asp Gly His Phe Leu Lys Thr
                165                 170                 175

Ser Cys Gly Ser Pro Asn Tyr Ala Ala Pro Glu Val Ile Ser Gly Lys
            180                 185                 190
```

-continued

```
Leu Tyr Ala Gly Pro Glu Val Asp Val Trp Ser Cys Gly Val Ile Leu
        195                 200                 205

Tyr Ala Leu Leu Cys Gly Thr Leu Pro Phe Asp Asp Glu Asn Ile Pro
    210                 215                 220

Asn Leu Phe Lys Lys Ile Lys Gly Gly Ile Tyr Thr Leu Pro Ser His
225                 230                 235                 240

Leu Ser Ser Glu Ala Arg Asp Leu Ile Pro Arg Met Leu Ile Val Asp
                245                 250                 255

Pro Val Lys Arg Ile Thr Ile Pro Glu Ile Arg Gln His Arg Trp Phe
            260                 265                 270

Gln Thr His Leu Pro Arg Tyr Leu Ala Val Ser Pro Pro Asp Thr Val
        275                 280                 285

Glu Gln Thr Lys Lys Ile Asn Glu Glu Ile Val Gln Glu Val Val Asn
    290                 295                 300

Met Gly Phe Asp Arg Asn Gln Val Leu Glu Ser Leu Arg Asn Arg Thr
305                 310                 315                 320

Gln Asn Asp Ala Thr Val Thr Tyr Tyr Leu Leu Leu Asp Asn Arg Phe
                325                 330                 335

Arg Val Pro Ser Gly Tyr Leu Glu Ser Glu Phe Gln Glu Thr Thr Asp
            340                 345                 350

Ser Gly Ser Asn Pro Met Arg Thr Pro Glu Ala Gly Ala Ser Pro Val
        355                 360                 365

Gly His Trp Ile Pro Ala His Val Asp His Tyr Gly Leu Gly Ala Arg
    370                 375                 380

Ser Gln Val Pro Val Asp Arg Lys Trp Ala Leu Gly Leu Gln Ser His
385                 390                 395                 400

Ala His Pro Arg Glu Ile Met Asn Glu Val Leu Lys Ala Leu Gln Glu
                405                 410                 415

Leu Asn Val Cys Trp Lys Lys Ile Gly His Tyr Asn Met Lys Cys Arg
            420                 425                 430

Trp Val Pro Gly Leu Ala Asp Gly Gln Asn Thr Met Val Asn Asn Gln
        435                 440                 445

Leu His Phe Arg Asp Glu Ser Ser Ile Ile Glu Asp Asp Cys Ala Met
    450                 455                 460

Thr Ser Pro Thr Val Ile Lys Phe Glu Leu Gln Leu Tyr Lys Ala Arg
465                 470                 475                 480

Glu Glu Lys Tyr Leu Leu Asp Ile Gln Arg Val Asn Gly Pro Gln Phe
                485                 490                 495

Leu Phe Leu Asp Leu Cys Ala Ala Phe Leu Thr Glu Leu Arg Val Ile
            500                 505                 510


<210> SEQ ID NO 3
<211> LENGTH: 512
<212> TYPE: PRT
<213> ORGANISM: tobacco

<400> SEQUENCE: 3

Met Asp Gly Ser Thr Val Gln Gly Gly Ser Ser Val Glu Ser Phe Leu
1               5                   10                  15

Asn Arg Tyr Lys Leu Gly Lys Thr Leu Gly Ile Gly Ser Phe Gly Lys
            20                  25                  30

Val Lys Ile Ala Glu His Thr Leu Thr Gly His Lys Val Ala Val Lys
        35                  40                  45

Ile Leu Asn Arg Arg Lys Ile Lys Asn Met Glu Met Glu Glu Lys Val
    50                  55                  60
```

-continued

```
Arg Arg Glu Ile Lys Ile Leu Arg Leu Phe Met His Pro His Ile Ile
65                  70                  75                  80

Arg Leu Tyr Glu Val Val Glu Thr Pro Ser Asp Ile Tyr Val Val Met
                85                  90                  95

Glu Tyr Val Lys Ser Gly Glu Leu Phe Asp Tyr Ile Val Glu Lys Gly
            100                 105                 110

Arg Leu Gln Glu Asp Glu Ala Arg Lys Phe Phe Gln Gln Ile Ile Ser
        115                 120                 125

Gly Val Glu Tyr Cys His Arg Asn Met Val Val His Arg Asp Leu Lys
    130                 135                 140

Pro Glu Asn Leu Leu Leu Asp Ser Lys Trp Asn Val Lys Ile Ala Asp
145                 150                 155                 160

Phe Gly Leu Ser Asn Ile Met Arg Asp Gly His Phe Leu Lys Thr Ser
                165                 170                 175

Cys Gly Ser Pro Asn Tyr Ala Ala Pro Glu Val Ile Ser Gly Lys Leu
            180                 185                 190

Tyr Ala Gly Pro Glu Val Asp Val Trp Ser Cys Gly Val Ile Leu Tyr
        195                 200                 205

Ala Leu Leu Cys Gly Thr Leu Pro Phe Asp Asp Glu Asn Ile Pro Asn
    210                 215                 220

Leu Phe Lys Lys Ile Lys Gly Gly Met Ile Ser Leu Pro Ser His Leu
225                 230                 235                 240

Ser Ala Gly Ala Arg Asp Leu Ile Pro Arg Met Leu Ile Val Asp Pro
                245                 250                 255

Met Lys Arg Met Thr Ile Pro Glu Ile Arg Met His Pro Trp Phe Gln
            260                 265                 270

Ala His Leu Pro Arg Tyr Leu Ala Val Pro Pro Pro Asp Thr Met Gln
        275                 280                 285

Gln Ala Lys Lys Ile Asp Glu Asp Ile Leu Gln Glu Val Val Lys Arg
    290                 295                 300

Gly Phe Asp Arg Asn Ser Leu Val Ala Ser Leu Cys Asn Arg Val Gln
305                 310                 315                 320

Asn Glu Gly Thr Val Ala Tyr Tyr Leu Leu Leu Glu Asn Gln Phe Arg
                325                 330                 335

Ala Ser Ser Gly Tyr Met Gly Ala Glu Phe Gln Glu Thr Met Glu Tyr
            340                 345                 350

Gly Tyr His Gln Ile Asn Ser Ser Glu Val Leu Leu Pro Cys Trp Gln
        355                 360                 365

His Leu Pro Gly Ile Met Asp Phe Gln Gln Val Gly Ala Arg Gln Phe
    370                 375                 380

Pro Val Glu Arg Lys Trp Ala Leu Gly Leu Gln Ser Arg Ala His Pro
385                 390                 395                 400

Arg Glu Ile Met Thr Glu Val Leu Lys Ala Leu Gln Gly Leu Asn Val
                405                 410                 415

Arg Trp Lys Lys Ile Gly Pro Tyr Asn Met Lys Cys Gln Trp Val Pro
            420                 425                 430

Gly Val Pro Gly His His Glu Gly Met Ser Asn Asn Ser Ile His Ile
        435                 440                 445

Gln Phe Phe Gly Asp Asp Ser Thr Val Ile Glu Asn Gly Gly Val Thr
    450                 455                 460

Ile Pro Asn Ala Val Lys Phe Glu Val Gln Leu Tyr Lys Thr Arg Glu
465                 470                 475                 480
```

-continued

```
Glu Lys Tyr Leu Leu Asp Leu Gln Arg Val Gln Gly Pro Gln Phe Leu
                485                 490                 495

Phe Leu Asp Leu Cys Ala Ala Phe Leu Ala Gln Leu Arg Val Leu Glx
            500                 505                 510


<210> SEQ ID NO 4
<211> LENGTH: 634
<212> TYPE: PRT
<213> ORGANISM: Saccharomyces cerevisiae

<400> SEQUENCE: 4

Met Ser Ser Asn Asn Asn Thr Asn Thr Ala Pro Ala Asn Ala Asn Ser
1               5                   10                  15

Ser His His His His His His His His His His His His His Gly His
            20                  25                  30

Gly Gly Ser Asn Ser Thr Leu Asn Asn Pro Lys Ser Ser Leu Ala Asp
        35                  40                  45

Gly Ala His Ile Gly Asn Tyr Gln Ile Val Lys Thr Leu Gly Glu Gly
    50                  55                  60

Ser Phe Gly Lys Val Lys Leu Ala Tyr His Thr Thr Thr Gly Gln Lys
65                  70                  75                  80

Val Ala Leu Lys Ile Ile Asn Lys Lys Val Leu Ala Lys Ser Asp Met
                85                  90                  95

Gln Gly Arg Ile Glu Arg Glu Ile Ser Tyr Leu Arg Leu Leu Arg His
            100                 105                 110

Pro His Ile Ile Lys Leu Tyr Asp Val Ile Lys Ser Lys Asp Glu Ile
        115                 120                 125

Ile Met Val Ile Glu Tyr Ala Gly Asn Glu Leu Phe Asp Tyr Ile Val
    130                 135                 140

Gln Arg Asp Lys Met Ser Glu Gln Glu Ala Arg Arg Phe Phe Gln Gln
145                 150                 155                 160

Ile Ile Ser Ala Val Glu Tyr Cys His Arg His Lys Ile Val His Arg
                165                 170                 175

Asp Leu Lys Pro Glu Asn Leu Leu Leu Asp Glu His Leu Asn Val Lys
            180                 185                 190

Ile Ala Asp Phe Gly Leu Ser Asn Ile Met Thr Asp Gly Asn Phe Leu
        195                 200                 205

Lys Thr Ser Cys Gly Ser Pro Asn Tyr Ala Ala Pro Glu Val Ile Ser
    210                 215                 220

Gly Lys Leu Tyr Ala Gly Pro Glu Val Asp Val Trp Ser Cys Gly Val
225                 230                 235                 240

Ile Leu Tyr Val Met Leu Cys Arg Arg Leu Pro Phe Asp Asp Glu Ser
                245                 250                 255

Ile Pro Val Leu Phe Lys Asn Ile Ser Asn Gly Val Tyr Thr Leu Pro
            260                 265                 270

Lys Phe Leu Ser Pro Gly Ala Ala Gly Leu Ile Lys Arg Met Leu Ile
        275                 280                 285

Val Asn Pro Leu Asn Arg Ile Ser Ile His Glu Ile Met Gln Asp Asp
    290                 295                 300

Trp Phe Lys Val Asp Leu Pro Glu Tyr Leu Leu Pro Pro Asp Leu Lys
305                 310                 315                 320

Pro His Pro Glu Glu Glu Asn Glu Asn Asn Asp Ser Lys Lys Asp Gly
                325                 330                 335

Ser Ser Pro Asp Asn Asp Glu Ile Asp Asp Asn Leu Val Asn Ile Leu
            340                 345                 350
```

-continued

```
Ser Ser Thr Met Gly Tyr Glu Lys Asp Glu Ile Tyr Glu Ser Leu Glu
        355                 360                 365

Ser Ser Glu Asp Thr Pro Ala Phe Asn Glu Ile Arg Asp Ala Tyr Met
    370                 375                 380

Leu Ile Lys Glu Asn Lys Ser Leu Ile Lys Asp Met Lys Ala Asn Lys
385                 390                 395                 400

Ser Val Ser Asp Glu Leu Asp Thr Phe Leu Ser Gln Ser Pro Pro Thr
                405                 410                 415

Phe Gln Gln Gln Ser Lys Ser His Gln Lys Ser Gln Val Asp His Glu
            420                 425                 430

Thr Ala Lys Gln His Ala Arg Arg Met Ala Ser Ala Ile Thr Gln Gln
        435                 440                 445

Arg Thr Tyr His Gln Ser Pro Phe Met Asp Gln Tyr Lys Glu Glu Asp
    450                 455                 460

Ser Thr Val Ser Ile Leu Pro Thr Ser Leu Pro Gln Ile His Arg Ala
465                 470                 475                 480

Asn Met Leu Ala Gln Gly Ser Pro Ala Ala Ser Lys Ile Ser Pro Leu
                485                 490                 495

Val Thr Lys Lys Ser Lys Thr Arg Trp His Phe Gly Ile Arg Ser Arg
            500                 505                 510

Ser Tyr Pro Leu Asp Val Met Gly Glu Ile Tyr Ile Ala Leu Lys Asn
        515                 520                 525

Leu Gly Ala Glu Trp Ala Lys Pro Ser Glu Glu Asp Leu Trp Thr Ile
    530                 535                 540

Lys Leu Arg Trp Lys Tyr Asp Ile Gly Asn Lys Thr Asn Thr Asn Glu
545                 550                 555                 560

Lys Ile Pro Asp Leu Met Lys Met Val Ile Gln Leu Phe Gln Ile Glu
                565                 570                 575

Thr Asn Asn Tyr Leu Val Asp Phe Lys Phe Asp Gly Trp Glu Ser Ser
            580                 585                 590

Tyr Gly Asp Asp Thr Thr Val Ser Asn Ile Ser Glu Asp Glu Met Ser
        595                 600                 605

Thr Phe Ser Ala Tyr Pro Phe Leu His Leu Thr Thr Lys Leu Ile Met
    610                 615                 620

Glu Leu Ala Val Asn Ser Gln Ser Asn Glx
625                 630
```

<210> SEQ ID NO 5
<211> LENGTH: 47
<212> TYPE: DNA
<213> ORGANISM: Arabidopsis thaliana

<400> SEQUENCE: 5
gcgctcgaga ccatggatca ttcatcaaat agatttggca ataatgg 47

<210> SEQ ID NO 6
<211> LENGTH: 27
<212> TYPE: DNA
<213> ORGANISM: Arabidopsis thaliana

<400> SEQUENCE: 6
gcgggatcct cagatcacac gaagctc 27

<210> SEQ ID NO 7
<211> LENGTH: 16
<212> TYPE: DNA
<213> ORGANISM: Arabidopsis thaliana -continued

```
<400> SEQUENCE: 7

gatgtatgga gttgcg                                                    16


<210> SEQ ID NO 8
<211> LENGTH: 17
<212> TYPE: DNA
<213> ORGANISM: Arabidopsis thaliana

<400> SEQUENCE: 8

cgcataggat tggaacc                                                   17
```

METHOD OF ENHANCING PLANT RESISTANCE TO GEMINIVIRUSES BY TRANSFORMATION WITH A SNF-1 POLYNUCLEOTIDE

CROSS-REFERENCE TO RELATED APPLICATION

Under 35 USC §119(e)(1), this application claims the benefit of prior U.S. provisional application No. 60/147,613, filed Aug. 6, 1999.

BACKGROUND

Plant pathogens are of great economic importance, as plant disease accounts for a significant fraction of crop losses. The present invention provides a method of making plants with enhanced resistance to infection with plant pathogens, including viral pathogens, bacterial pathogens, and fungal pathogens.

SUMMARY OF THE INVENTION

The present invention provides a method of preparing plants with enhanced resistance to infection with plant pathogens. The method comprises transforming a plant cell with a DNA construct which comprises an exogenous SNF-1 transgene, i.e., a DNA which encodes an SNF-1 protein kinase or the catalytic domain of such kinase. The transgene also comprises a promoter which regulates expression of the SNF-1 kinase or the catalytic domain. The promoter is operably linked to the DNA sequence which encodes the SNF-1 kinase or catalytic domain. The method further comprises the step of generating a transformed plant from the transformed plant cell. The transformed plant expresses the SNF-1 kinase or the catalytic domain and, thus, contains an SNF-1 kinase or catalytic domain that is encoded by the SNF-1 transgene as well as the SNF-1 kinase that is encoded by the plants own SNF-1 gene. Such plants are referred to as "overexpressors." The present method is especially useful for producing plants with enhanced resistance to plant pathogens, particularly viral pathogens, more particularly Geminiviruses. It is expected that the present method is also useful for producing plants with enhanced resistance to abiotic stress. Examples of abiotic stress are ozone, heat stress, and salt stress.

The present invention also provides a plant cell having a SNF-1 transgene stably integrated into its genome. The transgene comprises a DNA sequence encoding a SNF-1 kinase or the catalytic domain of such kinase and a promoter which controls expression of the DNA coding sequence in the plant cell. The present invention also relates to cell cultures consisting of such transformed cells, plants regenerated from such transformed cells and seeds of such transformed plants.

BRIEF DESCRIPTION OF THE FIGURES

FIG. 1 shows the nucleotide sequence, SEQ ID NO: 1, and amino acid sequence, SEQ ID NO:2, of SNF1 kinase from *Arabidopsis thaliana*. The cDNA was obtained from a two-hybrid screen and sequenced by standard methods. The sequence is identical to a previously reported SNF1 cDNA from the same species (Le Guen, L., Thomas, M., Bianchi, M., Halford, N. G., and Kreis, M. (1992) Structure and expression of a gene from Arabidopsis thaliana encoding a protein related to SNF1 protein kinase. Gene 120: 249–254).

FIG. 3. Mean latent period following Beet Curly Top Virus (BCTV) inoculation of transgenic antisense SNF1 plants. Non-transgenic *Nicotania. benthamiana* plants and plants representing three independent *N. benthamiana* transgenic lines expressing an antisense SNF1 construct (AS-4, AS-5, and AS-12) were agroinoculated with a standard dose of BCTV (OD600=1.0). The mean latent period (days post-inoculation) is indicated, and the number of infected versus inoculated plants for each treatment is given in parenthesis. Note that the latent period for BCTV on non-transgenic plants is approximately 21 days, whereas the latent period observed for the three transgenic lines tested in this experiment were approximately 14 days (lines AS-5 and AS-12) and 16 days (line (AS-4).

DETAILED DESCRIPTION OF THE INVENTION

The present method provides a method of transforming a plant cell which is useful for preparing a plant with enhanced resistance to plant pathogens, particularly viral pathogens, and to abiotic stress. The method of transforming the cell comprises the steps of introducing into a plant sample an exogenous DNA fragment which comprises a transgene comprising a sequence which encodes a SNF-1 kinase protein or the catalytic domain thereof and a promoter which is operably linked to SNF-1 kinase encoding sequence, i.e., the promoter controls expression of the SNF-1 kinase or catalytic domain. The cells are then grown under conditions that allow for expression of the SNF-1 kinase or SNF-1 catalytic domain, and, preferably, expression of a selectable or screenable marker gene that, preferably, is co-introduced into the plant sample with the SNF1 transgene. The marker gene may be on the same DNA fragment as the SNF-1 transgene or different DNA fragment.

Thereafter, cells which contain and express the SNF-1 transgene are selected and used to generate pathogen resistant transgenic plants. Expression of the transgene, preferably, is assayed by conventional techniques such as for example Northern analysis or RT-PCR. The transgenic plants produced in accordance with the present method contain the transgene within the genome of their cells, i.e., the transgenic plants are stably transformed. It has been determined that such transgenic plants are resistant to infection with geminiviruses, particularly Beet Curly Top Virus (BCTV). As used herein, the term "resistant", means a significant increase in the amount of geminivirus required to produce disease symptoms as compared to a similar non-transgenic plant which does not contain the transgene. In the case of the geminivirus BCTV, which infects dicotyledonous plants in over 70 different families, symptoms include curling and deformation of new leaves at the apex followed by severe stunting. In the case of the geminivirus, Tomato Golden Mosaic Virus (TGMV), which infects dolonaceous plants such as tobacco, tomato, and pepper, such disease symptoms include curling and deformation of new leaves at the shoot apex as well as the appearance of golden mosaic (yellow)areas in the affected leaves. Alternatively, resistance is monitored by assaying virus accumulation using conventional techniques such as Southern analysis using a viral DNA probe.

SNF-1 Kinase

Figure 2:
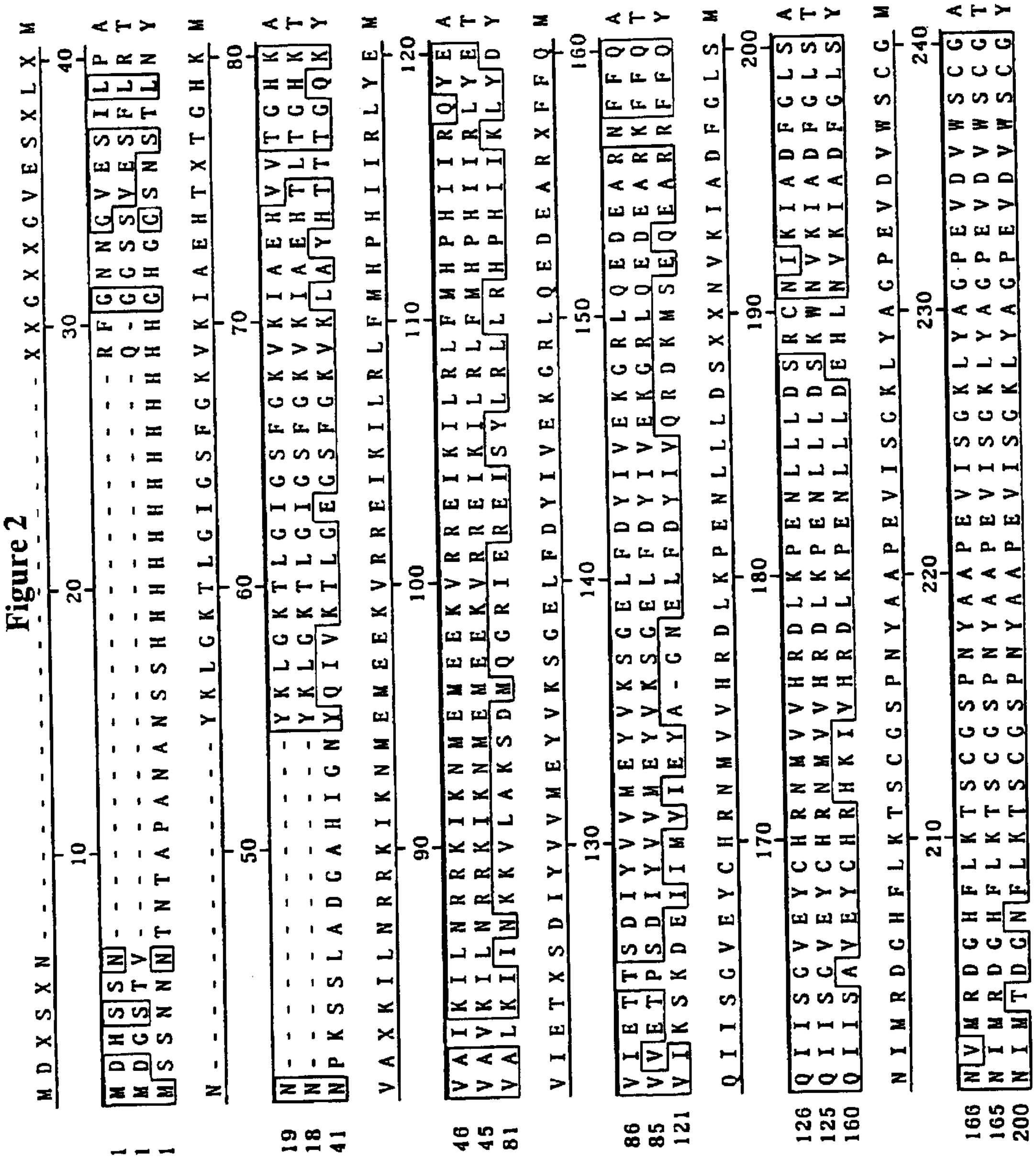
FIG. 2 shows an amino acid sequence alignment of SNF1 proteins from yeast, SEQ ID NO:4, Arabadopsis, SEQ ID NO:2, and tobacco, SEQ ID NO:3. The sequences shown were obtained from GenBAnk and aligned using the ClustalW algorithm.
Figure 2:
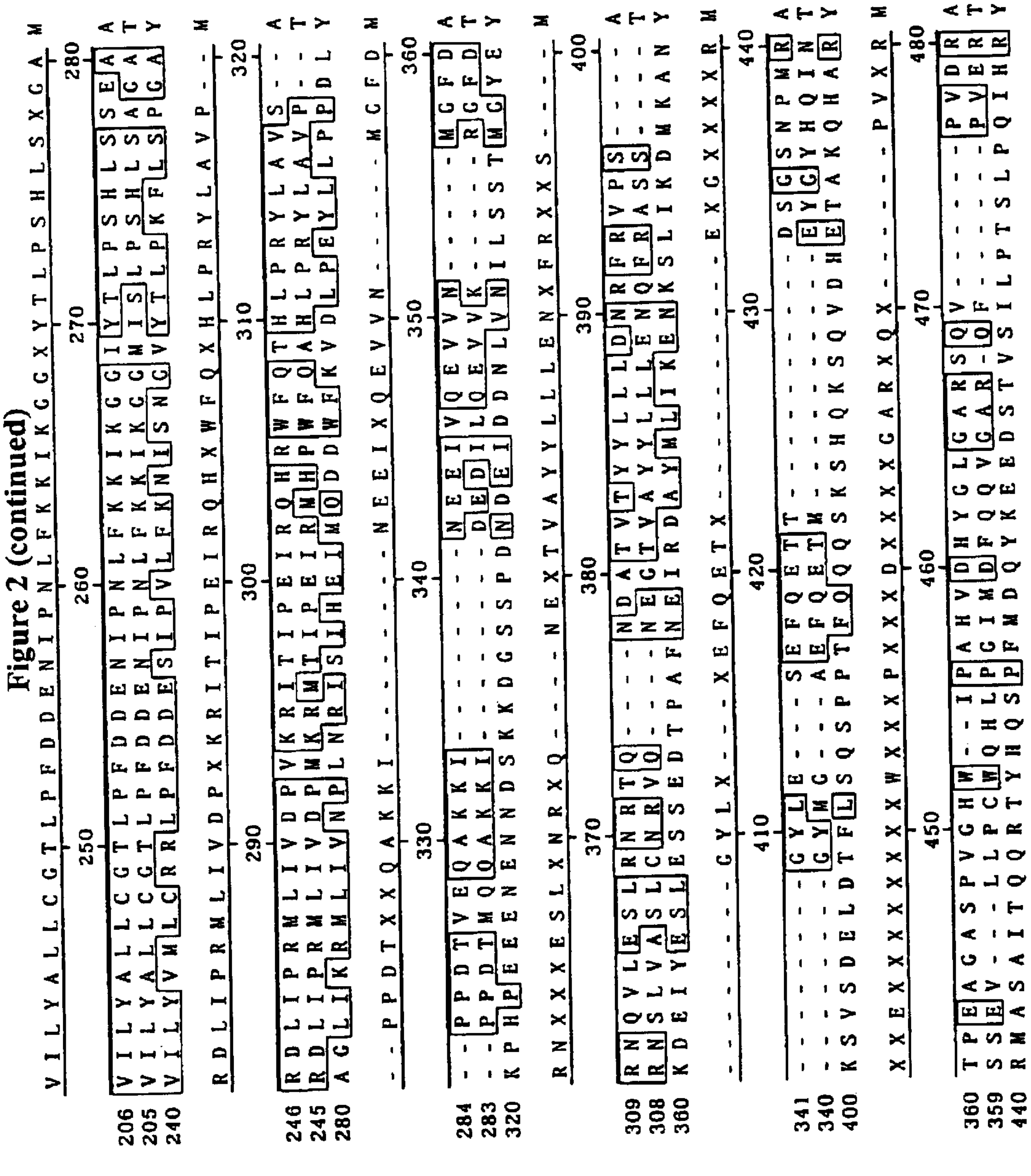
Figure 2:
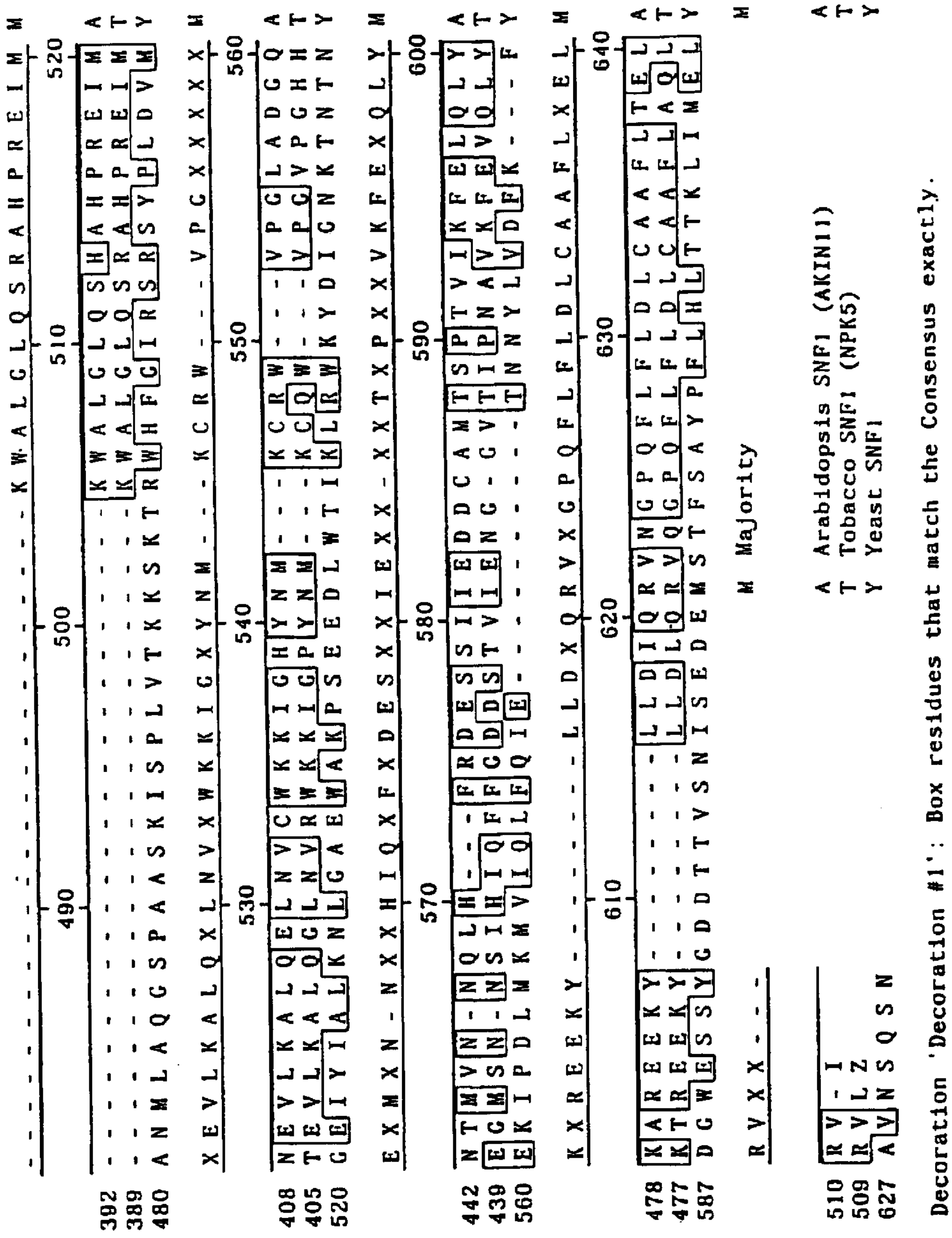

SNF1 is a serine/threonine kinase that plays a key role in glucose sensing and signal transduction pathways in yeast and plant cells. A similar role is ascribed to the homologous AMP-activated protein kinase (AMPK) in mammalian cells (for review see Johnston, M. (1999) Feasting, fasting, and fermenting: glucose sensing in yeast and other cells. Trends in Genetics 15: 29–33). In yeast, SNF1 kinase is required for the expression of glucose-repressed genes (e.g. SUC2, which encodes invertase, an enzyme that hydrolyzes sucrose to glucose and fructose). In addition to enzymes involved in carbohydrate metabolism, SNF1 kinase also regulates enzymes involved in lipid metabolism, and is also required for normal cell cycle control in yeast. Plant homologues have been cloned from Arabidopsis, tobacco, potato, barley, and rye. The amino acid sequences of the Arabidopsis and tobacco SNF-1 kinase are shown in FIG. 2. The tobacco and rye SNF1 proteins have been shown to complement yeast snf1 mutants, suggesting that the function of the SNF1 protein is conserved between yeast and plants.

SNF-1 Transgene

As used herein, a SNF-1 transgene is a polynucleotide having a sequence which encodes a protein whose amino acid sequence is at least 90% identical, preferably 95% identical, more preferably at least 97% identical to the amino acid sequence of a plant or yeast SNF-1 kinase or to the amino acid sequence of the catalytic domain of a plant or yeast SNF-1 kinase. For the SNF-1 transgenes which encode the truncated SNF-1 protein kinase, i.e., the catalytic domain, it is preferred that the coding sequence encode the N terminal portion of the plant or yeast SNF-1 kinase . For plant SNF-1 kinase, the preferred N terminal portion comprises from about amino acid 1 to about amino acid 350. For yeast SNF-1 kinase, the preferred N-terminal portion comprises from about amino acid 1 to about amino acid 400. Such N-terminal portion of the plant and yeast SNF1 proteins contains the putative ATP binding site as well as subdomains typically found in protein kinases.

The SNF-1 encoding sequence may be a heterologous SNF-1 encoding sequence, i.e., an SNF-1 gene from yeast or a different plant species. For example, a tobacco plant may be transformed with an SNF-1 gene from Arabidopsis. Alternatively, the encoding sequence may be a homologous SNF-1 kinase encoding sequence, i.e., an SNF-1 gene from the same plant species. For example, a tobacco plant may be transformed with an SNF-1 gene from another tobacco plant.

The protein encoded by the SNF-1 transgene need not have an amino acid sequence which is 100% identical to a known amino acid sequence, referred to hereinafter as a "reference sequence". Such protein may have an altered sequence in which one or more of the amino acids in the reference sequence is deleted or substituted, or one or more amino acids are inserted into the sequence of the reference amino acid sequence. As a result of the alterations, the altered protein has an amino acid sequence which is at least 90% identical to the reference sequence, preferably at least 95% identical, more preferably at least 97% identical, most preferably at least 99% identical to the reference sequence. Altered sequences which are at least 95% identical have no more than 5 alterations, i.e. any combination of deletions, insertions or substitutions, per 100 amino acids of the reference sequence. Percent identity is determined by comparing the amino acid sequence of the variant with the reference sequence using MEGALIGN project in the DNA STAR program. Sequences are aligned for identity calculations using the method of the software basic local alignment search tool in the BLAST network service (the National Center for Biotechnology Information, Bethesda, Md) which employs the method of Altschul, S. F., Gish, W., Miller, W., Myers, E. W. & Lipman, D. J. (1990) *J Mol. Biol.* 215, 403–410. Identities are calculated by the Align program (DNAstar, Inc.) In all cases, internal gaps and amino acid insertions in the candidate sequence as aligned are not ignored when making the identity calculation. The alterations are designed not to abolish the kinase activity of the altered protein or polypeptide.

While it is possible to have nonconservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

The transgene further comprises a promoter which is operably linked to the SNF-1 coding sequence for expression of the coding sequence. Preferably, the transgene further comprises a polyadenylation signal. The promoter, preferably, is a plant promoter, for example the 35S cauliflower mosaic virus (CaMV) promoter or a nopaline synthase or octopine synthase promoter. Examples of other constitutive promoters used in plants are the 19 S promoter, and promoters from genes encoding actin or ubiquitin. Optionally, the promoter is a regulatable or inducible promoter. One example of an inducible promoter is the chemically inducible promoter known as the tobacco PR-1a promoter. Another example of an inducible promoter is one which is wound inducible. Such promoters are described by Stanford et al., Mol. Gen. Genet. 215: 200–208 (1989); Xu et al., Plant Molec. Biol. 22: 573–588 (1993), Logemann et al., Plant Cell 1: 151–158 (1989); Rohrmeier & Lehle, Plant Molec. Biol. 22: 783–792 (1993); Firek et al., Plant Molec. Biol. 22: 129–142 (1993); and Warner et al., Plant J. 3: 191–201 (1993). Other suitable promoters include tissue specific promoters. Examples of such promoters are green tissue specific promoters, root specific promoters, stem specific promoters, and flower specific promoters such as those described by Hudspeth & Gurla, Plant Molec. Biol. 12: 579–589 (1989) and de Framond, FEBS 290: 103–106 (1991).

For the purposes of maximizing yield in crop plants, it may be desirable to control SNF1 expression in transgenic plants since gross overexpression of SNF1, in some cases, may prove toxic. Such control, preferably, is achieved by using promoters less active than the normally strong and constitutive 35S CaMV promoter, or by selecting 35S lines that are low level expressors. Additional control is also achieved by placing the transgene under the control of tissue specific and/or developmentally regulated promoters, or by using inducible promoters (e.g. a glucocorticoid-inducible promoter).

In addition to the transgene, the exogenous DNA fragment, preferably, also comprises other appropriate regulatory signals, such as a leader sequence, transcription terminator, and polyadenylation site, which direct expression of the operably linked SNF-1 coding sequence in the plant cell. Such regulatory signals are readily available in the art.

Plant Cell Transformation with the Transgene

Suitable plant cells are from monocotyledonous or dicotyledonous plant. Suitable monocotyledous species are, by way of example, barley, wheat, maize and rice. Suitable dicotyledonous species include, but are not limited to, tobacco, tomato, sunflower, petunia, cotton, sugarbeet, potato, lettuce, melon, soybean, canola and pepper. Thus, the method is useful for conferring enhanced pathogen resistance to a wide variety of plants. Agricultural crop plants are of particular importance. Any type or source of plant cells which serve as target for transformation by one or more delivery methods can serve as the host cells for transformation. Such sources include, by way of example, immature and mature embryos, pollen, protoplasts, suspension.

Delivery of the DNA fragment in to the host plant cells may be accomplished by a variety of techniques available in the art. Such techniques include non-biological mechanisms such as microprojectile bombardment, electroporation, microinjection, induced uptake, and aerosol beam injection.

Optionally, the DNA construct comprising the exogenous SNF-1 transgene may be subcloned into a vector effective for introducing the DNA construct into the plant. Ti plasmid vectors effective for this purpose are pMON 530, pBI221, pGMVNEO pCMC1100, and pDG208. In a preferred embodiment, the DNA construct is subcloned into a binary Ti plasmid plant vector and mobilized into *Agrobacterium. Tumefaciens*, and the *A. Tumefaciens* transformnant is then used for infection and transformation plant cells or tissues. Binary plant transformation vectors are known in the art Preferably, the SNF1 gene cloned in a Ti plasmid vector is introduced into the plant sample using an Agrobacterium transformant. The Agrobacterium transformant is cocultivated with plant cells or plant tissues. The Agrobacterium binds to the plant cell walls and transfers the plasmid or a portion thereof into the plant cell. Where the vector is *Agrobacterium tumefaciens*, transformation results from the transfer of a specific portion of the plasmid, referred to hereinafter as "T-DNA", into the genome of plant cells. The T-DNA is transferred and integrated into the plant genome as a discrete unit. The T-DNA contains the exogenous SNF-1 gene or the catalytic domain thereof, which, preferably, is flanked by a promoter and polyadenylation signals. Preferably, the T-DNA also contains a screenable marker gene, or selectable marker resistance gene, such as Tn5 neomycin phosphotransferase II, which confers resistance to kanarnycin.

The transformed plant cells are selected by growth in selection medium. Thereafter, transformed plants are regenerated from the cells using conventional techniques and analyzed to ensure that the transformed plant contains the exogenous gene and is expressing the exogenous gene.

Leaf discs or tissue cultures of transformed plant cells are propagated to generate transformed whole plants. The transformed leaf discs or plant cell are cultured on a suitable medium, preferably, a selectable growth medium. Plants may be regenerated from the resulting callus. Transgenic plants are those whose cells stably integrate the exogenous transgene into their genome, the exogenous gene being expressible in the cells. Resistance or sensitivity of the transgenic plant to a pathogen is assessed by the ability of the plants to grow, grow faster, or avoid disease symptoms in the presence of a predetermined dose or inoculum of the pathogen as compared to plants of the same species which have not been transformed in accordance with the present method.

Enhanced Susceptibility of Plants Expressing Antisense Arabidopsis SNF-1 Kinase Our interest in SNF1 kinase began with the discovery that two geminiviral proteins, TrAP (AL2) from tomato golden mosaic virus, and L2 protein from beet curly top virus, interact with SNF1 kinase. We further found that transgenic *Nicotiana benthamiana* plants expressing full-length or truncated versions of the viral proteins show enhanced susceptibility (ES) to virus infection, characterized by a decreased latent period (time to appearance of disease symptoms) and reduced $ID_{50}$ values (inoculum dose required to infect 50% of plants in a given sample). Interestingly, these transgenic plants show ES not only to the DNA-containing geminiviruses TGMV and BCTV, but also to the RNA virus tobacco mosaic virus, indicating that the ES phenotype is quite general and may extend to all viruses, bacterial pathogens, fungal pathogens, and abiotic stress. We hypothesized that one function of the TrAP and L2 proteins during the geminiviral infection process is to inhibit the activity of SNF1 kinase, thereby disabling a general host defense. To test our hypothesis we attempted to reproduce the ES phenotype by expressing an antisense SNF1 kinase construct (driven by the CaMV 35S promoter) in transgenic plants. Transgenic *N. benthamiana* plants comprising the exogenous Arabidopsis SNF-1 gene in antisense orientation relative to the 35S promoter were tested by challenge inoculation with BCTV. Viruses were delivered to plants by the agroinoculation procedure described in Elmer et al. (1988) *Agrobacterium-mediated inoculation of plants with tomato golden mosaic virus DNAS*. Plant Mol. Biol. 10:225–234.

Figure 4:
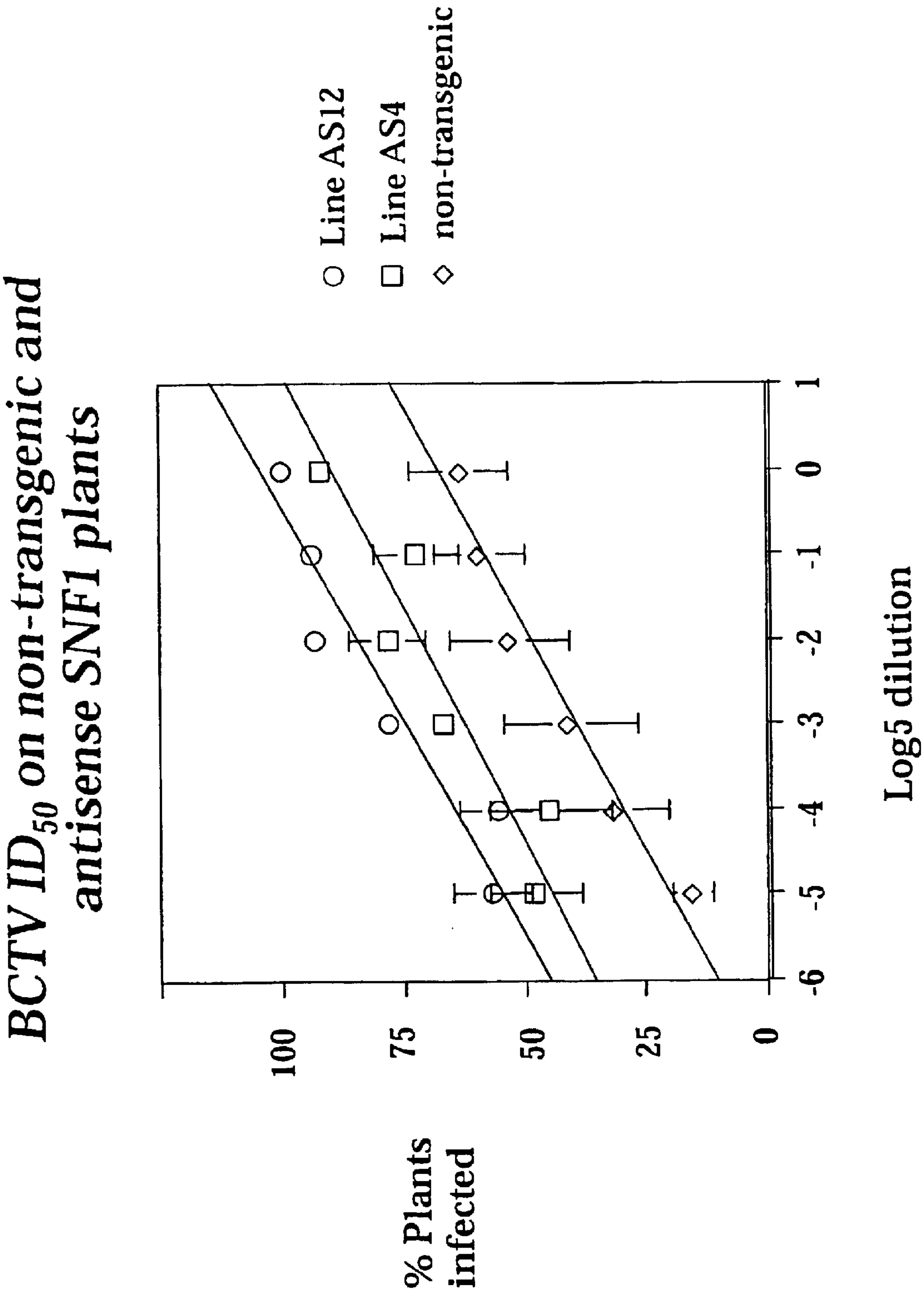
FIG. 4. BCTV $ID_{50}$ of non-transgenic and antisense SNF1 plants. Non-transgenic *N. benthamiana* plants and plants representing two independent transgenic lines expressing an antisense SNF1 construct (AS-4 and AS-12) were agroinoculated with varying doses BCTV, beginning with the standard dose (OD600=1.0) followed by serial 5-fold dilutions of the standard dose. The percent of plants in the sample infected at each inoculum dose was noted and plotted versus the log5 of the dilution. The data represent the average of three independent experiments, with 16 plants for each treatment in each experiment. Note that the $ID_{50}$ for BCTV on non-transgenic plants is reached at approximately 18-fold dilution of the inoculum, whereas the $ID_{50}$ is reached at 1,150-fold dilution in line AS-4, and following 6,250-fold dilution in line AS-12.

The data shown in FIGS. 3 and 4 show that the ES phenotype does in fact result following expression of antisense SNF1 kinase in transgenic *N. benthamiana* plants. The ES phenotype is characterized by a reduction in mean latent period of from 5–7 days (FIG. 3), and a reduction in viral $ID_{50}$ from 60- to 330-fold (FIG. 4), depending on the transgenic line. Clearly, infection levels comparable to those seen with non-transgenic plants can be achieved with much less virus inoculum in the case of the transgenic antisense SNF1 lines.

EXAMPLE 1

Transgenic Plants Expressing an Exogenous SNF-1 Transgene

A. Cloning of Arabidopsis SNF-1 gene

The nucleotide sequence, SEQ ID NO: 1, and amino acid sequence, SEQ ID NO:2, of SNF1 kinase from *Arabidopsis thaliana* are shown in FIG. 1.

The SNF1 gene was obtained in a yeast two-hybrid screen using a truncated TGMV TrAP protein as bait, and an Arabidopsis cDNA library as prey. The cDNA was full-length, and was recognized as encoding SNF1 by virtue of its homology to yeast SNF1 and to the tobacco SNF1 proteins (FIG. 2), and by its identity to previously cloned Arabidopsis SNF1 (Le Guen, L., Thomas, M., Bianchi, M., Halford, N. G., and Kreis, M. (1992) Structure and expression of a gene from *Arabidopsis thaliana* encoding a protein related to SNF1 protein kinase. Gene 120: 249–254). (FIG. 1 and 2).

The SNF1 gene was cloned from the yeast two-hybrid vector by PCR using GCGCTCGAGACCATGGATCATT-CATCAAATAGATTTGGCAATAATGG, SEQ ID NO: 5, as the 5' primer and GCGGGATCCTCAGATCACACGAA-GCTC, SEQ ID NO: 6, as 3' primer. The 5' primer adds an XhoI site to the 5' end of the SNF1 sequence, while the 3' primer adds a BamHI site. The PCR product was subsequently cleaved with XhoI and BaniHI and cloned into the similarly cleaved, plasmid vector pET3 (Clonetech).

In addition to obtaining SNF1 from a two-hybrid clone as described above, it should be possible to obtain SNF1 cDNA by RT-PCR from any species in which the SNF1 sequence is known such as for example, tobacco, and potato, barley and rye. The sequences of the known SNF1 genes are generally available on a publically available database such as GenBank.

To create recombinant Ti plasmids for agrobacterium-mediated plant transformation, the Ti plasmid vector pMON530 was cut with SmaI and treated with calf intestinal alkaline phosphatase to prevent re-ligation. The SNF1 sequence was then removed from pET by cutting with NdeI (from the pET3 polylinker) and BamHI, and rendered flush ended by treatment with T4 DNA polymerase. The flush-ended pMON530 and SNF1 DNA fragments were mixed and ligated, and used to transform *E. coli*. Clones containing the SNF1 gene in the sense and antisense orientation relative to the 35S promoter in pMON530 were selected and mated into *A. tumefaciens* for transformation of plants.

B. Materials and Methods Used to Prepare *A. tumefaciens* Transformant

The binary system consists of two components: 1) a disarmed *A. tumefaciens* Ti plasmid, which provides functions required for excision of the T-DNA from the Ti plasmid, and for its transfer and integration into the plant genome and 2) a second, smaller binary plasmid vector of about 6–10 kb that contains the T-DNA to be transferred, i.e. the Arabadopsis SNF-1 gene and a drug resistance gene.

Cultures of *E. coli* harboring the binary vectors were grown in LB broth containing 50 μg/ml spectinomycin. The binary vectors contained the Arabadopsis SNF-1 transgene and a selectable marker. Many binary vectors also include a streptomycin/spectinomycin resistance gene (outside the T-DNA) for selection in *E. coli* and *A. tumefaciens*. The binary vector employed was pMON530 prepared as described in (Rogers et al. (1987) *Improved vectors for plant transformation: Expression cassette vectors and new selectable markers*. Methods in Enzymology 153: 253–277).

Non-transformed *A. tumefaciens* containing the resident, disarmed Ti plasmid was obtained from Monsanto. Cultures of the non-transformed *A. tumefaciens* were grown overnight in LB broth containing 25 μg/ml chloramphenicol and 50 μg/ml kanamycin. Cultures of *E. coli* containing the mobilization plasmid (e.g. pRK2013) were grown overnight in LB broth containing 50 μg/ml kanamycin. Cultures of *E. coli* containing the binary plasmid were grown overnight in LB broth containing 50 μg/ml spectinomycin.

1–2 drops of each overnight culture were mixed and streaked on an LB plate containing no selection marker. The plates were incubated at 28° C. until colonies appeared, usually for about 6 days. Then a small amount of culture was recovered from the LB plate and streaked on LB plates containing the selection markers or antibiotics which corresponded to the resistance markers of the *A. tumefaciens* recipient containing the disarmed Ti plasmid and the binary vector to select *A. tumefaciens* transformants.

The plates were incubated at 28° C. until colonies were detected on the plates. Several individual colonies were recovered from each plate and inoculated into LB broth containing the same antibiotics as the plate and incubate at 28° C. with shaking.

C. Transforming Plant Samples

Plasmid DNA was isolated from *A. tumefaciens* transform ants according to the method of Dhaese et al. (1979) Nucleic Acids Research 7: 1837 and used to verify the presence and integrity of Arabidopsis SNF-1 gene in T-DNA by Southern blot analysis or PCR.

*A. tumefaciens* transformants were also used to transform leaf discsfrom *Nicoliana benthamiana* plants. This step varies depending on the species to be transformed. For petunia and tobacco leaf discs are also used. For tomato, cotyledon pieces are used. For *Arabidopsis thaliana*, sterile root pieces are used. Prior to transformation, the plant tissues are sterilized in a solution of 20% Clorox, 0.5% Tween 20 for 15 min.

The leaf discs were placed upside down on MS 104 plates and preincubated for 48 hours at room temperature in continuous light to increase the transformation efficiency Thereafter, the sterilized leaf discs were soaked in a liquid culture of an *A. tumefaciens* transformant. This is done by placing 10–20 discs in a sterilin tube (with a loose cap) and adding 1 ml of an overnight culture. The discs were then removed, blotted dry with sterile filter paper, and placed upside down on an MS104 plate with no selection. After 48 hr on the non-selective MS104 media at room temperature, the discs were transferred to MS104 plates containing selection medium (750 μg/ml carbenicillin to kill the Agrobacterium and 300 μg/ml kanamycin to select for the desired T-DNA marker). After about 1–2 weeks, the discs form callus around the edges of the disc. This is followed by the appearance of shoots.

Shoots were removed at regular intervals from the callus and transferred to rooting media (MSO plates containing the antibiotics present in the MS104 plates). Shoots with roots were transferred to sterile soil in pots and covered with clear plastic to retain humidity. After 2–4 days, plastic can be removed and transgenic plants treated as normal plats.

Transformed leaf discs are harvested and analyzed for presence of SNF1 transgene and mRNA after 2–6 days.

Alternatively transformed regenerants are obtained and analyzed in the same manner. DNA, RNA or protein is isolated from the leaf discs or regenerated plants by conventional methods. The presence of an integrated SNF-1 transgene in the genome of the plant is examined by restriction endonuclease digestion followed by Southern blot analysis, or by PCR using primers designed to recognize T-DNA border sequences or by PCR using primers designed to amplify a region within the transgene. Expression of RNA encoding the SNF-1 transgene is examined by Northern blot analysis or by RT-PCR. Expression of protein is examined by Western blotting.

Transgenic lines are established by selfing transformed plants to homozygosity using conventional techniques.

The presence of sense transgenes in plants from lines S-1, S-2, S-3, S-5, and S-6 was verified by PCR, using the following primers: GATGTATGGAGTTGCG, SEQ ID NO; 7, and CGCATAGGATTGGAACC, SEQ ID NO:8. These primers lie within the SNF1 gene itself, and they amplified a fragment of about 500 bp from plants representing each of the transgenic lines. In addition, the transgenic plants are kanamycin resistant and seeds are routinely germinated on medium containing kanamycin. Kan resistance is conferred by the Ti plasmid vector. Further, non-transgenic plants are kan sensitive, and the primers do not amplify anything when non-transgenic plant DNA is used as template for PCR.

Northern blot analysis, using as probe band isolated and random primer labeled Arabidopsis SNF1 gene, showed a transcript of about 2 kb in RNA isolated from antisense and sense transgenic plants of all lines. The blots were done under high stringency conditions, so a signal from the endogenous tobacco SNF1 transcript(s) was not seen. There was no signal in RNA from control, non-transgenic plants.

D. Enhanced Resistance of Transgenic Plants Overexpressing (Sense) Arabidopsis SNF1 Kinase Transgenic *N. benthamiana* plants made as described above and comprising the exogenous Arabadopsis SNF-1 gene in sense orientation relative to the 35S promoter were tested by challenge inoculation with BCTV. Viruses were delivered to plants by the agroinoculation procedure described in Elmer et al. (1988) *Agrobacterium-mediated inoculation of plants with tomato golden mosaic virus DNASs* Plant Mol. Biol. 10: 225–234.

Figure 5:
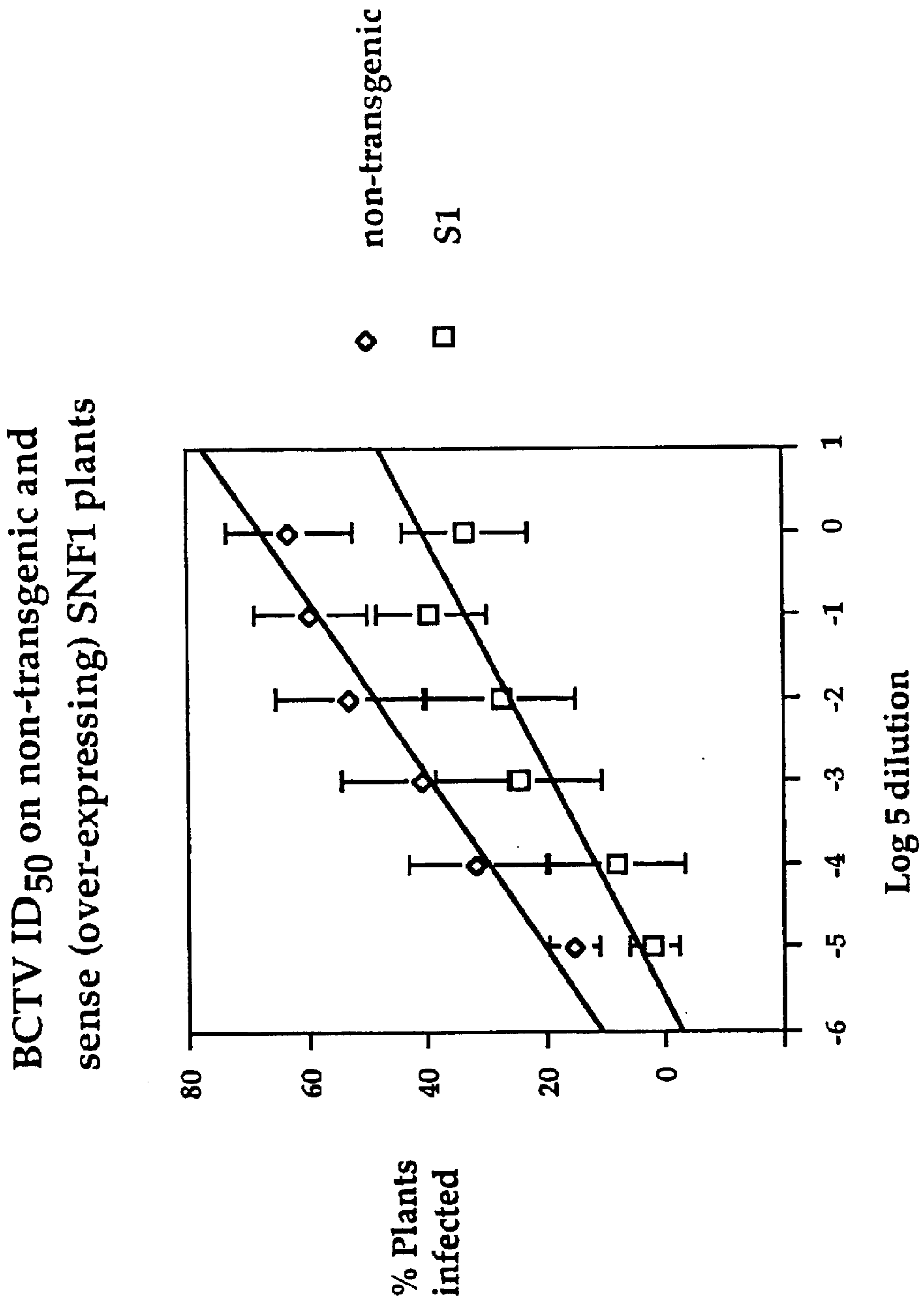
FIG. 5 is a graph showing BCTV $ID_{50}$ values on non-transgenic and a sense (overexpressing) SNF1 line. Non-transgenic *N. benthamiana* plants and plants representing a transgenic line expressing a sense SNF1 construct (S-1) were agroinoculated with varying doses of BCTV, beginning with the standard dose (OD600=1.0) followed by serial 5-fold dilutions of the standard dose. The percent of plants in the sample infected at each inoculum dose was noted and plotted versus the log5 of the dilution. The data represent the average of four independent experiments, with 16 plants for each treatment in each experiment. Note that the $ID_{50}$ for BCTV on non-transgenic plants is reached at approximately 18-fold dilution of the inoculum, whereas an inoculum greater than the standard dose is needed to achieve the $ID_{50}$ for line S-1.

Non-transgenic *N. benthamiana* plants and plants representing three transgenic lines expressing an sense SNF1 construct (S-1, S-3, and S-5) were agroinoculated with varying doses of BCTV, beginning with the standard dose (OD600=1.0) followed by serial 5-fold dilutions of the standard dose. The percent of plants in the sample infected at each inoculum dose was noted and plotted versus the log5 of the dilution. The data represent the average of four independent experiments, with 16 plants for each treatment. As shown in FIG. 5, the $ID_{50}$ for BCTV on non-transgenic plants was reached with essentially undiluted inoculum in this experiment, whereas the an inoculum greater than the standard dose is needed to achieve the $ID_{50}$ for lines S-1, S-3, and S-5. However, it is possible to calculate by extrapolation that a dose approximately 5-fold greater (line S-5), 13-fold greater (line S-3), and more than 200-fold greater (line S1) than the standard dose is needed to achieve 50% infection of transgenic plant populations.

Thus, in the case of transgenic, sense, over-expressing SNF1 lines, it is clear that the $ID_{50}$ is much greater than it is on non-transgenic plants (FIG. 5). That is, much more virus is required to infect a significant fraction of the transgenic plants. The plants prepared as described in the present example also had a slow growth phenotype, suggesting that use of a strong constitutive promoter such as CaMV 35 S may, in some cases, be less preferred.

While the method for preparing a transgenic plant which is more resistant to infection with a plant pathogen has been described to some degree of particularity, various adaptations and modifications can be made without departing from the scope of the invention as defined in the appended claims.

What is claimed is:

1. A method of producing a transformed plant cell, comprising:

introducing into a plant cell a DNA construct comprising a polynucleotide which is operably linked to a promoter, wherein said polynucleotide restores the catalytic activity to yeast snf1 mutants and encodes a protein kinase which confers resistance to infection by Geminivirus in a transformed plant cell, and wherein said protein kinase comprises an amino acid sequence that shares at least 90% sequence identity with a SNF-1 protein kinase having an amino acid sequence selected from the group consisting of SEQ ID NO:2, SEQ ID NO:3, and SEQ ID NO:4; wherein said protein kinase is expressed in said plant cell.

2. The method of claim 1 wherein the DNA construct further comprises a polynucleotide encoding a screenable marker or a selectable marker.

3. A method of preparing a transgenic plant with enhanced resistance to Geminivirus, said method comprising;

(a) providing a transformed plant cell comprising a a DNA construct comprising a polynucleotide which is operably linked to a promoter, wherein said polynucleotide restores the catalytic activity to yeast snf1 mutants and encodes a protein kinase which confers resistance to infection by Geminivirus in a transformed plant cell, and wherein said protein kinase comprises an amino acid sequence that shares at least 90% sequence identity with a SNF-1 protein kinase having an amino acid sequence selected from the group consisting of SEQ ID NO:2, SEQ ID NO:3, and SEQ ID NO:4; wherein said protein kinase is expressed in said plant cell; and (b) regenerating a transgenic plant from said transformed plant cell, wherein said transgenic plant is more resistant to infection by Geminivirus than a non-transgenic plant of the same species.

4. The method of claim 1 wherein the plant call is from Arabidopsis, tobacco, potato, barley, wheat maize, rice, tomato, rye, and soybean.

5. The method of claim 1, wherein said SNF-1 kinase is endogenous to the species of the plant cell and comprises an amino acid sequence that shares at least 90% amino acid sequence identity with a SNF-1 kinase that comprises an amino acid sequence selected from the group consisting of SEQ ID NO:2 and SEQ ID NO:3.

6. The method of claim 1, wherein said SNF-1 kinase is endogenous to a plant species that is different from the species of the plant cell and comprises an amino acid sequence that shares at least 90% amino acid sequence identity with a SNF-1 kinase that comprises an amino acid sequence selected from the group consisting of SEQ ID NO:2 and SEQ ID NO:3.

7. The method of claim 1, wherein said SNF-1 kinase is endogenous to yeast and comprises an amino acid sequence that shares at least 90% amino acid sequence identity with a SNF-1 kinase that comprises the amino acid sequence of SEQ ID NO:4.

8. A method of producing a transformed plant cell, comprising:

introducing into a plant cell a DNA construct comprising a polynucleotide which is operably linked to a promoter, wherein said polynucleotide encodes a protein kinase which confers resistance to infection by Geminivirus in a transformed plant cell, and wherein said protein kinase has an N-terminal catalytic domain with an amino acid sequence that is at least 90% identical to the N-terminal catalytic domain of a SNF-1 Protein kinase selected from the group consisting of SEQ ID NO: 2, SEQ ID NO:3, and SEQ ID NO:4, wherein the N-terminal catalytic domain of said SNF-1 protein kinase extends from amino acids 1 through 350 of SEQ ID NO:2 and SEQ ID NO:3, and amino acids 1 through 400 of SEQ ID NO:4.

* * * * *